United States Patent
Hanson et al.

(10) Patent No.: US 7,056,019 B1
(45) Date of Patent: Jun. 6, 2006

(54) QUALITY ASSURANCE PHANTOM SYSTEM

(76) Inventors: Todd Hanson, 2945C E. Bay Dr., #132, Largo, FL (US) 33771; James N. Marsh, 13909 Egret La., Clearwater, FL (US) 33762

(*) Notice: Subject to any disclaimer, the term of this patent is extended or adjusted under 35 U.S.C. 154(b) by 39 days.

(21) Appl. No.: 10/726,730

(22) Filed: Dec. 3, 2003

Related U.S. Application Data (63) Continuation-in-part of application No. 10/277,393, filed on Oct. 22, 2002, now abandoned.

(51) Int. Cl.
*G01D 18/00* (2006.01)

(52) U.S. Cl. .......................... 378/207; 378/18

(58) Field of Classification Search ............... 378/18, 378/65, 207; 250/252.1
See application file for complete search history.

(56) References Cited

U.S. PATENT DOCUMENTS

| | | | | | |
|---|---|---|---|---|---|
| 3,867,638 | A | * | 2/1975 | Golden | 378/145 |
| 5,511,107 | A | * | 4/1996 | Sliski | 387/207 |
| 6,231,231 | B1 | * | 5/2001 | Farrokhnia et al. | 378/207 |
| 6,364,529 | B1 | * | 4/2002 | Dawson | 378/207 |
| 6,493,574 | B1 | * | 12/2002 | Ehnholm et al. | 600/429 |

* cited by examiner

*Primary Examiner*—Edward J. Glick
*Assistant Examiner*—Jurie Yun
(74) *Attorney, Agent, or Firm*—Edward P. Dutkiewicz (57) ABSTRACT

A phantom system provides for the testing of diagnostic machines in a safe and efficient manner. First provided is a transparent cubic test device having a cylindrical aperture extending all the way to the rear face. The test device has a plurality of centered lines, making four equal squares on each face of the test system. There is a plurality of small bores positioned at all intersections of the scored white lines. A probe cylinder may receive and hold a probe. The cube has additional apertures to hold tissue testing and calibrating devices.

5 Claims, 11 Drawing Sheets

QUALITY ASSURANCE PHANTOM SYSTEM

RELATED APPLICATIONS

This application is a Continuation-in-Part Application of application Ser. No. 10/277,393, filed on Oct. 22, 2002, now abandoned.

FIELD OF THE INVENTION

The present invention relates to a quality assurance phantom system and more particularly pertains to calibrating a variety of devices involved in the treatment of patients. The present invention allows a user to test and calibrate beam emitting devices, such as Computer Assisted Tomography machines, X-ray machines, PET Scanners and MRI scanners.

DESCRIPTION OF THE PRIOR ART

The use of medical systems of known designs and configurations is known in the prior art. More specifically, medical systems previously devised and utilized for the purpose of calibrating or testing the accuracy of medical systems are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 4,344,183 issued Aug. 10, 1982, to Jacobson discloses a tool for computer assisted tomographic scanner. U.S. Pat. No. 5,095,499 issued Mar. 10, 1992, to Wentz discloses an oriented mammography phantom. U.S. Pat. No. 4,613,754 issued Sep. 23, 1986, to Vinegar et al. discloses a tomographic calibration apparatus. U.S. Pat. No. 5,506,884 issued Apr. 9, 1996, to Goodenough et al. discloses a radiation phantom and test methods employing the same. U.S. Pat. No. 4,126,789 issued Nov. 21, 1978, to Vogl et al. discloses an x-ray phantom. U.S. Pat. No. 4,649,561 issued Mar. 10, 1987, to Arnold discloses a test phantom and method of use of same. U.S. Pat. No. 4,988,866 issued Jan. 29, 1991, to Westerlund discloses a measuring device for checking radiation fields from treatment machines for radiotherapy. U.S. Pat. No. 6,369,381 issued Apr. 9, 2002, to Troxler et al. discloses an apparatus and method for calibration of nuclear gauges. U.S. Pat. No. 6,267,502 issued Jul. 31, 2001, to McNeirney et al. discloses alignment verification device and method of using the same with a visual light beam and an x-ray. U.S. Pat. No. 5,793,835 to Blanck issued Aug. 11, 1998, discloses quality assurance phantom for tomography and method of use. Finally, U.S. Pat. No. 6,364,529 issued Apr. 2, 2002, to Dawson discloses a radiation phantom.

While these devices fulfill their respective, particular objectives and requirements, the aforementioned patents do not describe a quality assurance phantom system that allows for the calibrating of a variety of medical beam emitting devices involved in the treatment of patients.

In this respect, the quality assurance phantom system according to the present invention substantially departs from the conventional concepts and designs of the prior art, and in doing so provides an apparatus primarily developed for the purpose of calibrating a variety of devices involved in the treatment of patients.

Therefore, it can be appreciated that there exists a continuing need for a new and improved quality assurance phantom system which can be used for calibrating a variety of medical diagnostic and treatment devices involved in the diagnosis and treatment of patients. In this regard, the present invention substantially fulfills this need.

SUMMARY OF THE INVENTION

In view of the foregoing disadvantages inherent in the known types of medical systems of known designs and configurations now present in the prior art, the present invention provides an improved quality assurance phantom system. As such, the general purpose of the present invention, which will be described subsequently in greater detail, is to provide a new and improved quality assurance phantom system and method which has all the advantages of the prior art and none of the disadvantages.

To attain this, the present system essentially comprises a medical diagnostic or treatment device, such as a computer assisted tomography scanner to provide internal imaging of a desired treatment area. An X-ray producing device may also be utilized to provide radiation to a desired treatment area.

The system also comprises a cubic test device formed of a transparent material. The test cube can have any one of a variety of dimensions, but the test cube as described in this preferred embodiment has a length of 14 centimeters and a height of 14 centimeters and a width of 14 centimeters. The test device has a front face, a rear face, a bottom face, a top face and a pair of side faces, each being equally sized and each having an edge. Each face of the six faces of the cube has a pair of etched lines dividing the face up into four equally sized squares. The lines are known as the central grid lines and are perpendicular to each other, and are equally spaced from the edges of the cube. The central grid lines intersect in the middle of each of the faces of the cube thereby dividing the cube face into four quadrants. Where each central grid line meets the edge of the cube, there is a notch indicating the mid-point of that face. The face of the cube also has four peripheral grid lines etched there into. The lines are at right angle to each other, parallel the edge and four centimeters in from the edge of the cube. The peripheral grid lines intersect near the four corners of the face of the cube, on each of the faces. The grid lines are equidistant from the edge of the cube. A 10 square centimeter square is formed on the cube face where the peripheral grid lines intersect each other and the central grid lines. The front face has a centrally located cylindrical aperture extending all the way to the rear face forming an aperture there through. The rear face of the test cube device also has four equally spaced recesses there into, with the recesses being configured to receive and hold any one of a plurality of testing cylinders. The testing cylinders each have a specific density to mimic specific tissue density. The test device also has a plurality of small bores, known as pin holes, positioned at all intersections of the central and peripheral grid lines.

Next provided is a probe cylinder that is configured to be received and held within the central aperture. The probe cylinder is adapted to receive the probe of the radiation detecting and measuring device. The probe is configured and sized to couple within the central cylindrical aperture of the cubic test device.

Next provided is a test device resting table. The resting table has a flat plane surface to receive the cubic test device. The flat plane surface also has a plurality of indicia to enable a user to locate the test cube in the center of the resting table. The resting table has a first central finger adapted to couple with a central bore on the bottom face of the cubic test device to prevent the cubic test device from sliding on the resting table. The resting table further has a plurality of leveling screws and a recess aperture on one side.

Next provided is a test device level. The test device level has a generally rectilinear configuration with an upper surface and a lower surface and two opposing ends with an edge disposed there between. The level has a plurality of sized recesses therein on the upper surface of each end of the level. The upper surface recesses each enclose a round radio-opaque sphere. The level also has a recess on each end with an enclosed radio-opaque pin contained therein. Each of the ends of the level has indicia inscribed thereon. The level has a pair of studs coupled to the lower surface of the level. The studs each having an associated o-ring coupled thereto. The level has a second central finger to couple with the recess aperture of the resting table. This coupling holds the resting table in place.

Next provided is a ruler. The ruler is configured with indicia to enable the user to measure any discrepancies between a projected beam and the scored white central and peripheral grid lines of the cube thereby allowing for re-centering of the appropriate components.

Also provided is a universal machine alignment tool. The tool is used to provide a standard centering on any one of a plurality of commercially available patient resting surfaces, such as an X-ray table surface. The alignment tool comprises several components in combination. The tool has a central locking component. The central locking component has a flat lower portion having an upper surface and a lower surface. The central locking component also has two sides and two top lips. The tool has an upwardly opened C-shaped configuration with the two sides having an upper end and a lower end and being oppositely located and upwardly projecting. The lower end of each of the sides is coupled with the flat lower portion of the central locking component. At the top end of each of the sides is a top lip. The top lips are oppositely located. The C-shaped configuration forms a rectangularly shaped passageway there through. The flat lower portion has two threaded upwardly projecting locking lug studs. The upper surface of the lower portion has a plurality of indicia and a centrally located alignment pin aperture. Another component of the alignment tool is a pair of table side end clamps. Each clamp has a generally T-shaped configuration with a flat table edge lip coupled at right angles to a rectilinearly shaped adjustable portion. Each adjustable portion has a slot there through. Also provided is a pair of locking lug nuts sized to be received by the threaded locking lug studs of the flat lower portion of the central locking component. In operation the alignment tool is set upon a flat patient surface. The locking nuts are releases and the clamps are slid apart until the side edges of the patient surface has been accommodated. The clamps are then pressed firmly against the sides of the patient surface and the locking nuts are tightened A plurality of density plugs are provided. The density plugs have varying densities to imitate the density of various body compartments. One density plug has the density of bone, another water, another of an inflated lung and another of a deflated lung. The density plugs allow a user to test beam strength against a standard density.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved quality assurance phantom system which has all of the advantages of the prior art medical systems of known designs and configurations and none of the disadvantages.

It is another object of the present invention to provide a new and improved quality assurance phantom system which may be easily and efficiently manufactured and marketed.

It is further an object of the present invention to provide a new and improved quality assurance phantom system which is of durable and reliable constructions.

An even further object of the present invention is to provide a new and improved quality assurance phantom system which is susceptible of a low cost of manufacture with regard to both materials and labor, and which accordingly is then susceptible of low prices of sale to the consuming public, thereby making such quality assurance phantom system economically available to the buying public.

Even still another object of the present invention is to provide a quality assurance phantom system for calibrating a variety of devices involved in the treatment of patients through the use of lasers.

Lastly, it is an object of the present invention to provide a new and improved quality assurance phantom system with a computed tomography scanner to provide internal imaging of a desired treatment area, a linear accelerator with a probe to provide radiation to the desired treatment area, a treatment planning system with an associated laser to provide a visual image of where treatment is being projected, and a transparent cubic test device having a cylindrical aperture extending all the way to the rear face. The test device has a centered internally scribed cube, a plurality of surface scored white lines forming intersections and dissecting the test device into six equal cubes, and a plurality of small bores positioned at all intersections of the scored white lines. A probe cylinder receives the probe of the linear accelerator. The combination of the probe cylinder and the probe of the linear accelerator couples within the cylindrical aperture of the cubic test device.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
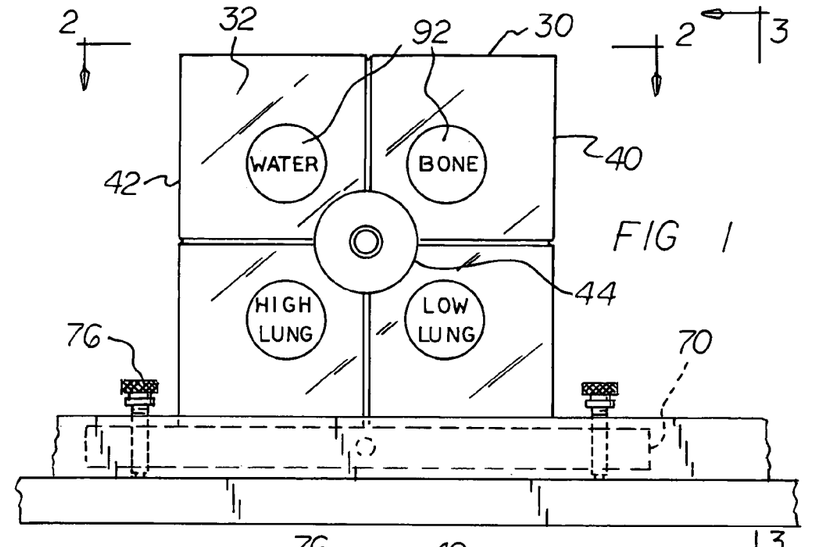
FIG. 1 is a front elevational view of the quality assurance phantom system constructed in accordance with the principles of the present invention.
Figure 2:
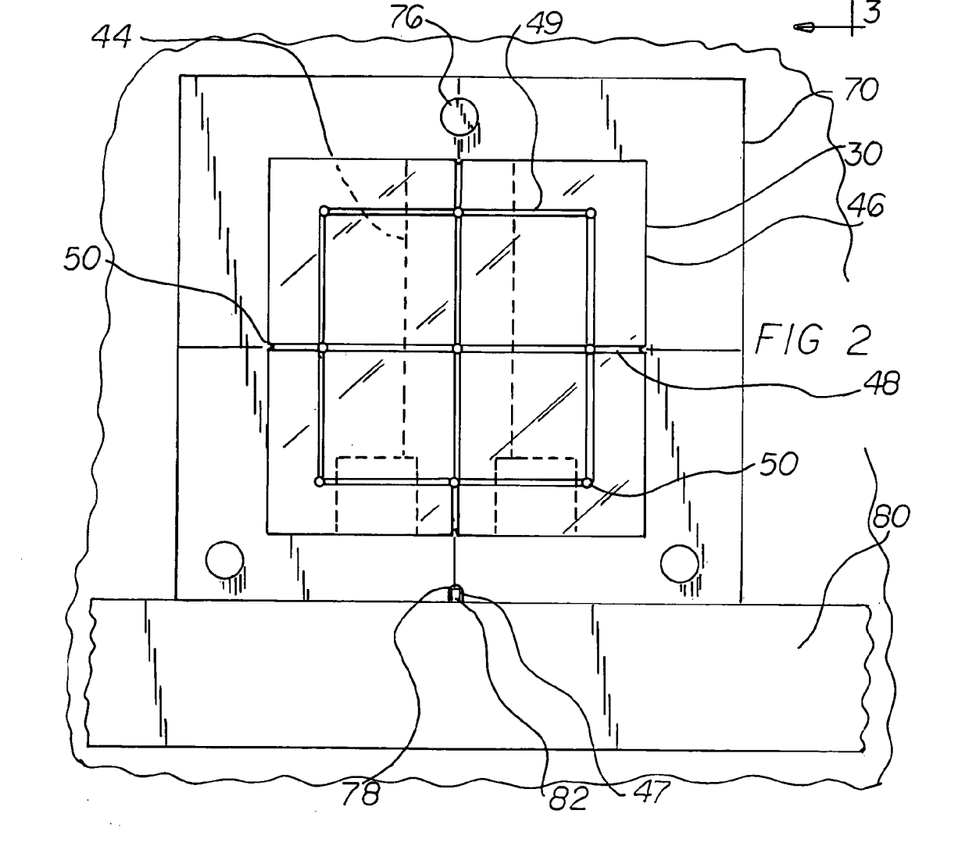
FIG. 2 is a top plan view of the system taken along line 2—2 of FIG. 1.
Figure 3:
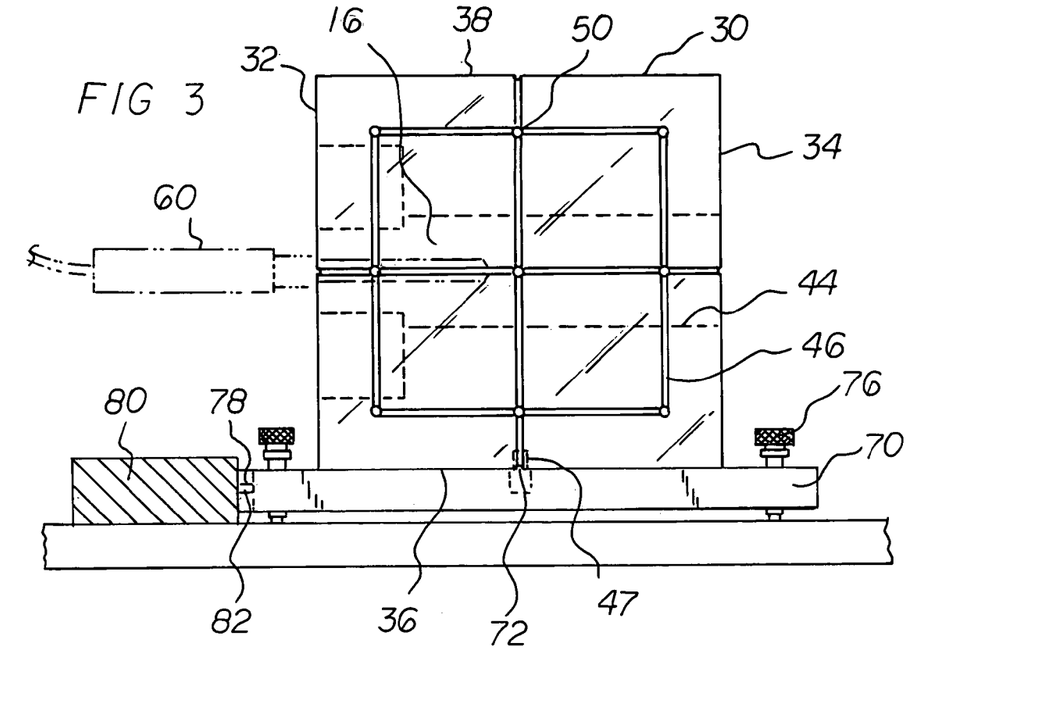
FIG. 3 is a side elevational view of the system taken along line 3—3 of FIG. 1.

With reference now to the drawings, and in particular to FIG. 1 thereof, the preferred embodiment of the new and improved quality assurance phantom system embodying the principles and concepts of the present invention and generally designated by the reference numeral 10 will be described.

Figure 10:
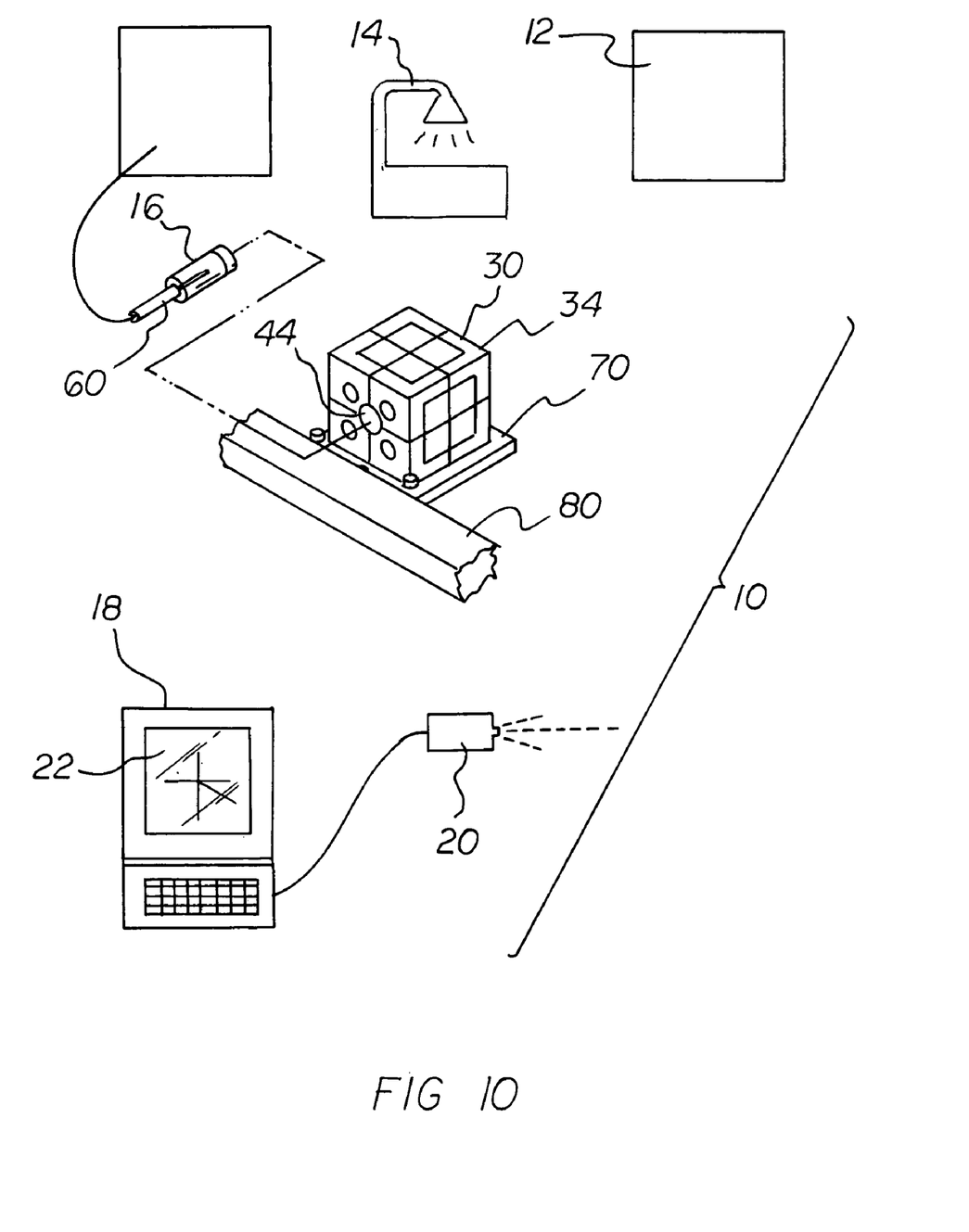
FIG. 10 is a schematic illustration of the electrical components of the system of the present invention.

The present invention, a medical device phantom standardizing system 10 to allow a user to safely and conveniently test and standardize diagnostic and treatment equipment and machines that provide or use beam energy, such as an CT scanner 12 or a MRI scanner, or X-ray machine 14. A Laser 20 may be used, as is in the case for visual alignment of beam projection or in conjunction with a quality assurance program 18. The laser may be used in conjunction with a display system 22 to enable the visualization of the beam projection. Such components are individually configured and correlated with respect to each other so as to attain the desired objective. The system comprises several components in combination.

Figure 11:
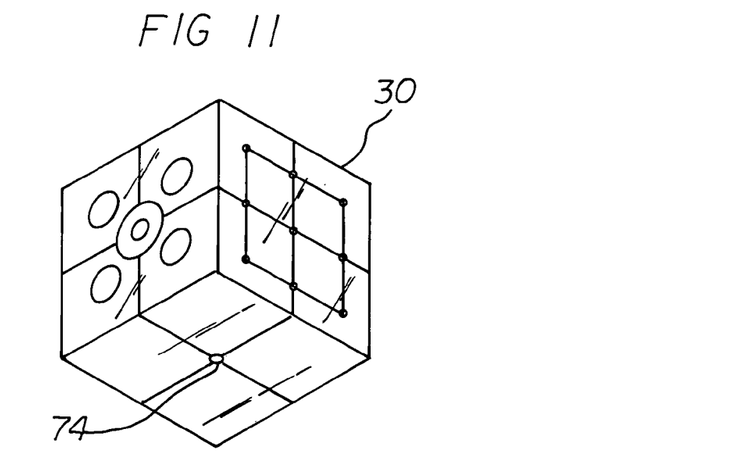
FIG. 11 is a perspective illustration of the cubic test device showing the central bore.

First provided is a cubic test device 30. The cubic test device, or test cube, is formed of a transparent material. The test cube has a front face 32, a rear face, 34, a bottom face 36, a top face 38 and a pair of side faces 40, 42. Each face is equally sized and each has four edges. The faces of the cube are 14 centimeters in length, but in alternate embodiments, can be any size.

Each face of the six faces of the cube has a pair of etched lines, also known as the central grid lines 48, one being horizontal and the other being vertical. The grid lines are located a first distance from the cube edge. The lines thereby divide the face into four equally sized squares. The lines are perpendicular to each other and are equally spaced from the edges of the cube. The central grid lines intersect in the center point of each of the faces of the cube, thereby dividing each of the cube faces into four quadrants.

The cube has a centrally located notch 47 on the lower edge of the cube side. The central grid line meets the edge of the cube at the notch thereby indicating the mid-point of that face.

The face of the cube also has four peripheral grid lines 49 etched there into. The lines are located at right angles to each other and parallel to the edge of the cube. The peripheral grid lines are located a second distance from the edge of the cube. The peripheral grid lines intersect near the four corners of the face of the cube, on each of the faces of the cube. The grid lines are equidistant from the edge of the cube, whereby a plurality of squares 46 are formed on each of the cube faces, where the peripheral grid lines intersect each other and intersect the central grid lines.

The front face of the cube has a centrally located cylindrical aperture 44 extending all the way to the rear face forming an aperture there through. The rear face of the cube also has four equally spaced recesses there into. The recesses are configured to receive and hold any one of a plurality of testing cylinders. The testing cylinders each have a specific density to mimic specific tissue density. The test cube also has a plurality of small bores 50, known as pin holes, positioned at all intersections of the central and peripheral grid lines.

Figure 5:
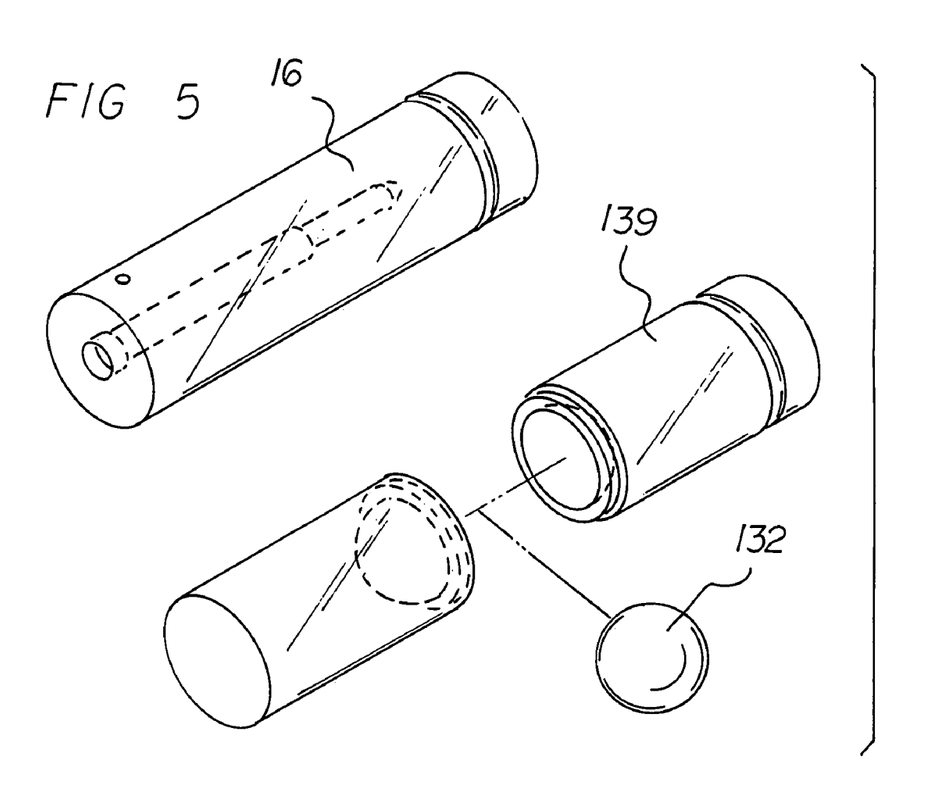
FIG. 5 is a perspective and an exploded perspective view of a probe cylinder adapted to receive the probe of the linear accelerator.

Next provided is a probe cylinder 16. The probe cylinder is configured to be received by and held within the central aperture. The probe cylinder configured to receive the probe 60 of a radiation detecting and measuring device. The probe is configured and sized to couple within the central cylindrical aperture of the cubic test device.

Next provided is a test device resting table 70. The resting table has a flat plane surface having four sides, the plane surface configured to receive the cubic test device. The flat plane surface also has a plurality of indicia to enable a user to locate the test cube in the center of the resting table. The resting table has a first central finger 72 configured to couple with a central bore 74 on the bottom face of the cubic test device. The coupling of the first central finger and the central bore of the bottom of the cube prevents the cubic test device from sliding on the resting table. The resting table has a plurality of leveling screws 76 and a recess aperture 78 on one side. The recess aperture and the first central finger provide a duplicatable location of the test cube on the resting table.

Figure 13:
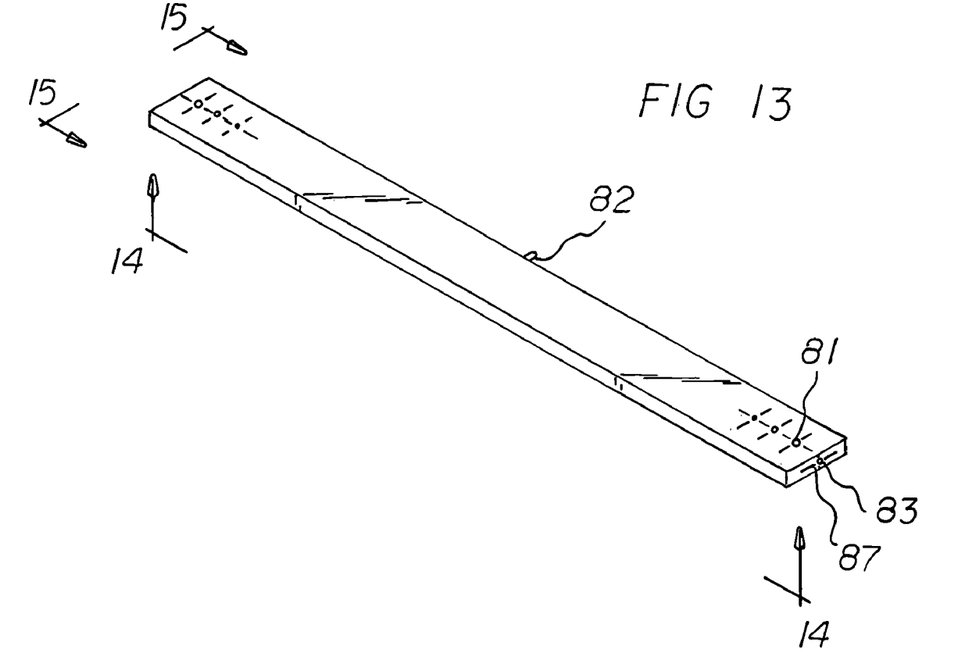
FIG. 13 is a perspective illustration of the test device level.
Figure 14:
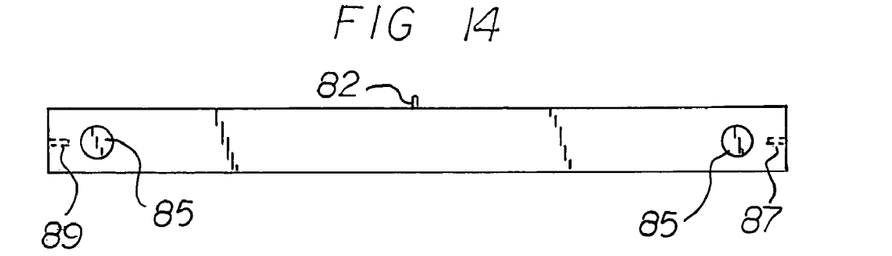
FIG. 14 is a bottom view of the test device level taken at line 14—14 of FIG. 13.
Figure 15:
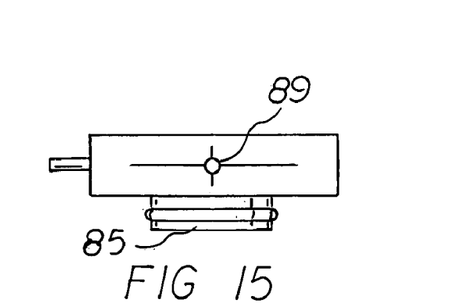
FIG. 15 is an end view of the test device level taken alone line 15—15 of FIG. 13.
Figure 16:
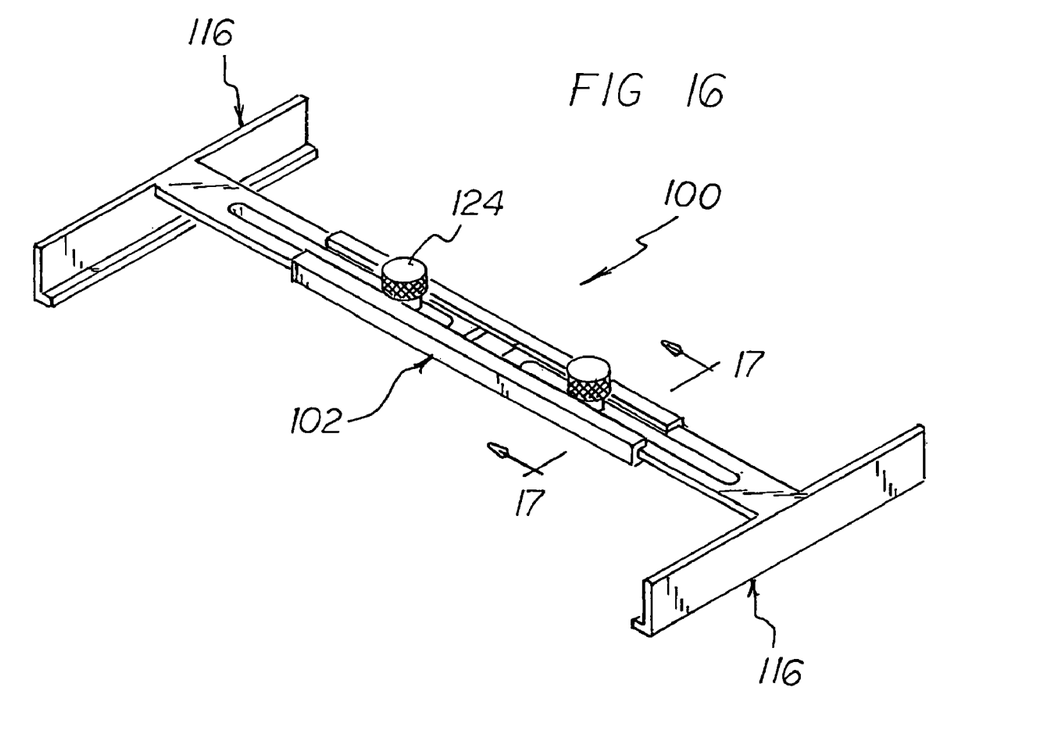
FIG. 16 is a perspective illustration of the machine alignment tool.
Figure 17:
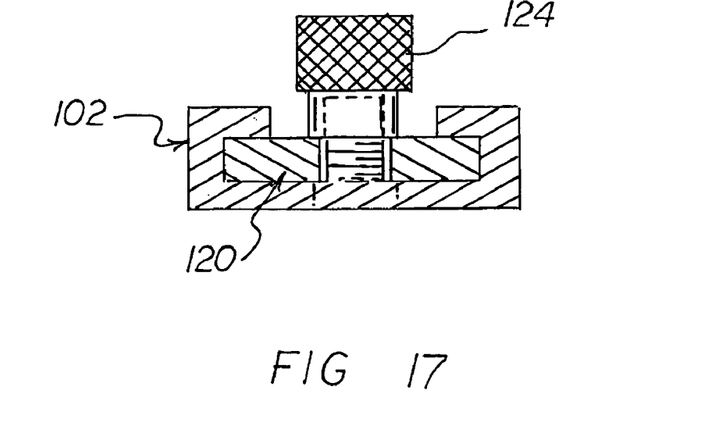
FIG. 17 is a cross sectional view of the machine alignment tool taken along line 17—17 of FIG. 16.
Figure 18:
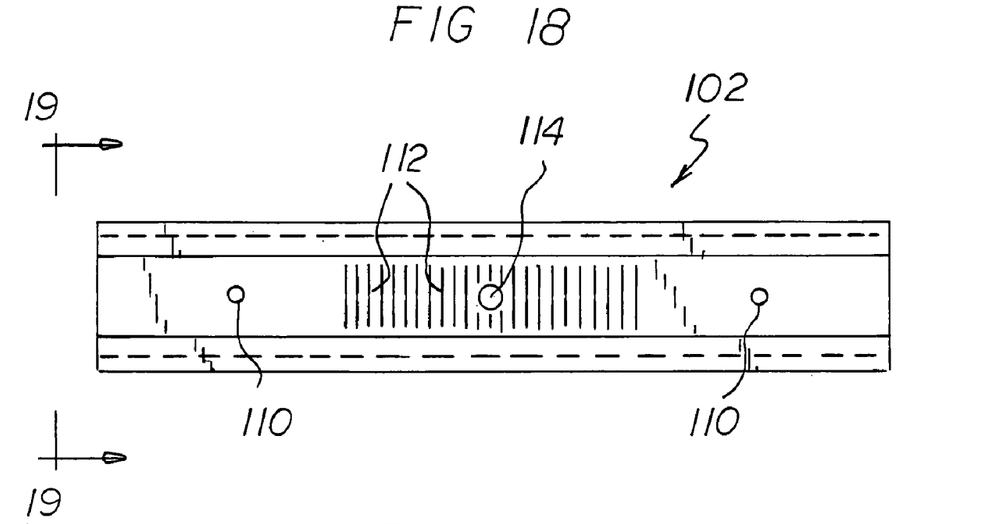
FIG. 18 is a plan view of the locking component of the tool.
Figure 19:
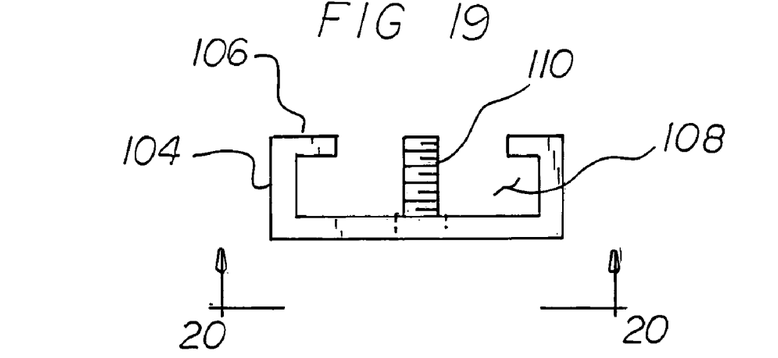
FIG. 19 is an end view of the locking component of the tool taken along line 19—19 of FIG. 18.
Figure 20:
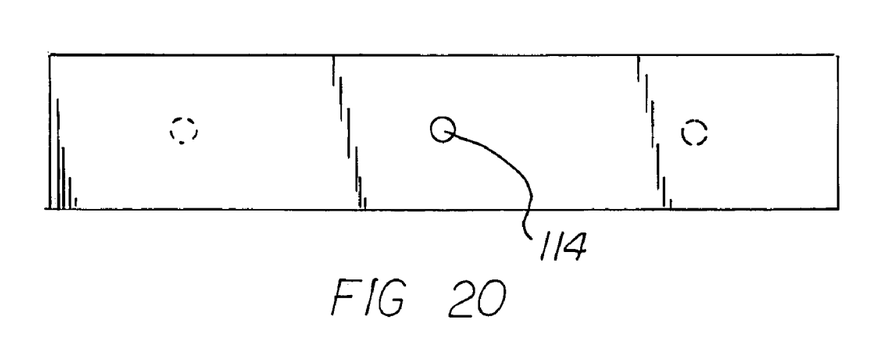
FIG. 20 is a bottom view of the locking component of the tool taken along line 20—20 of FIG. 19.
Figure 21:
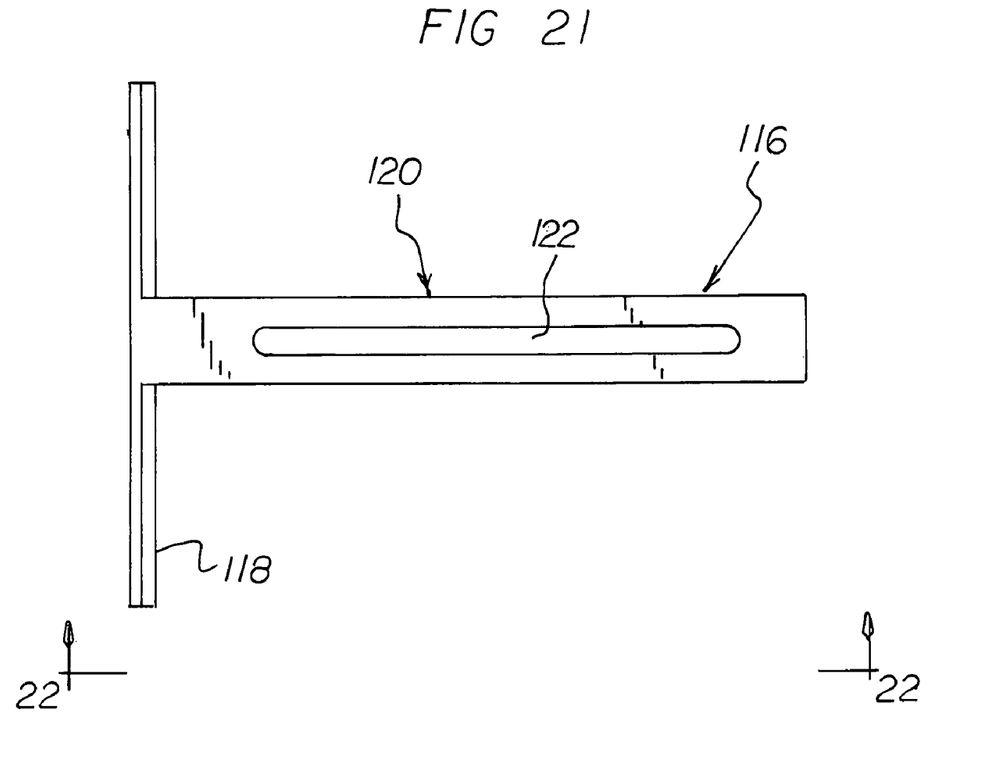
FIG. 21 is a plan view of the cable side end clamp of the alignment tool.
Figure 22:
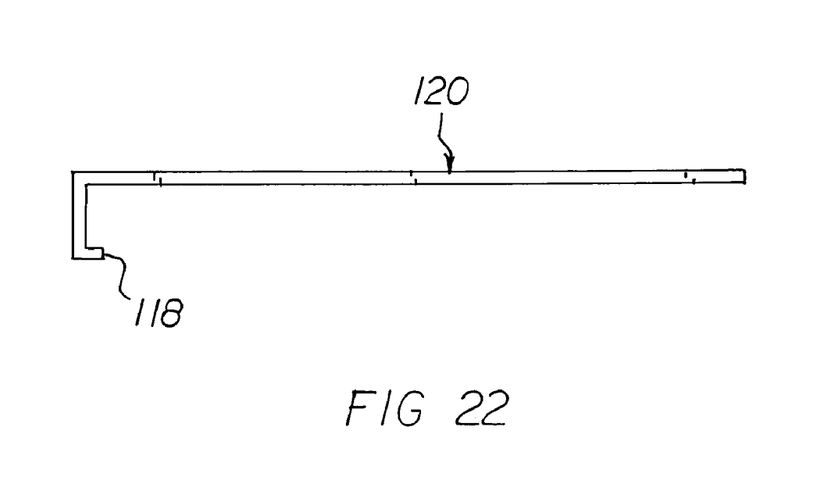
FIG. 22 is an end view of the table side end clamp of the alignment tool taken along line 22—22 of FIG. 21.

Next provided is a test device level 80. The test device level has a generally rectilinear configuration with an upper surface and a lower surface and two opposing ends with an edge disposed there between. The level has a plurality of sized recesses 81 therein on the upper surface of each end of the level. The upper surface recesses each enclose a round radio-opaque sphere. The level also has a recess 83 on each end with an enclosed radio-opaque pin 89 contained therein. Each of the ends of the level has indicia inscribed thereon. The level has a pair of studs 85 coupled to the lower surface of the level. The studs each having an associated o-ring 87 coupled thereto. The level has a second central finger 82 to couple with the recess aperture of the resting table. This coupling holds the resting table in place.

Figure 6:
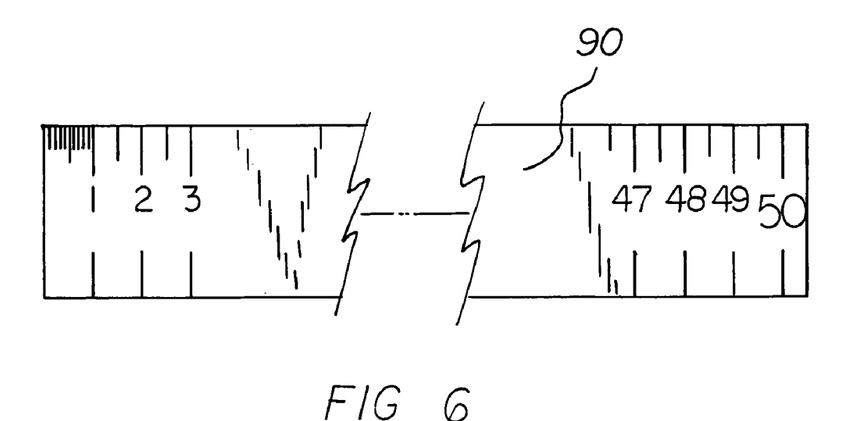
FIG. 6 is a front elevational view of the ruler adapted to measure discrepancies between the laser and the scored white lines.
Figure 7:
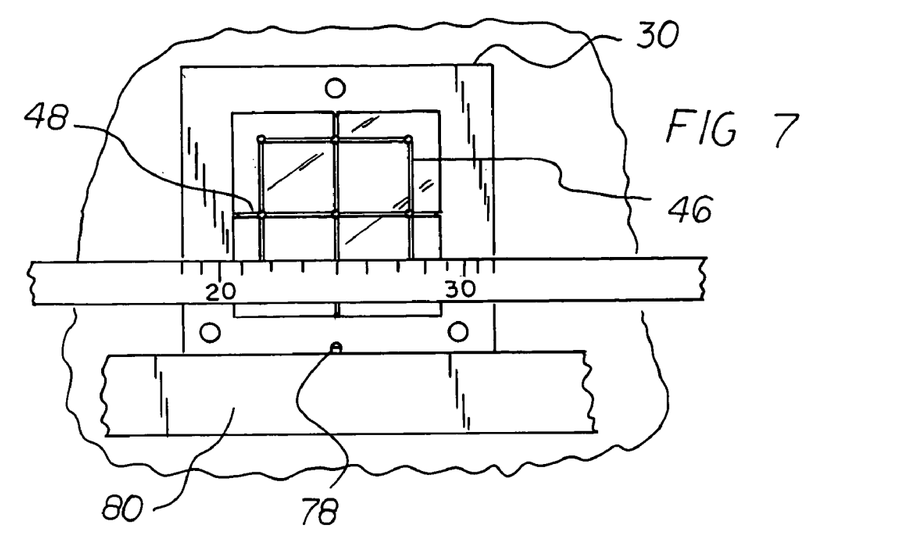
FIG. 7 is a top plan view similar to FIG. 2 but illustrating the measuring of discrepancies.
Figure 8:
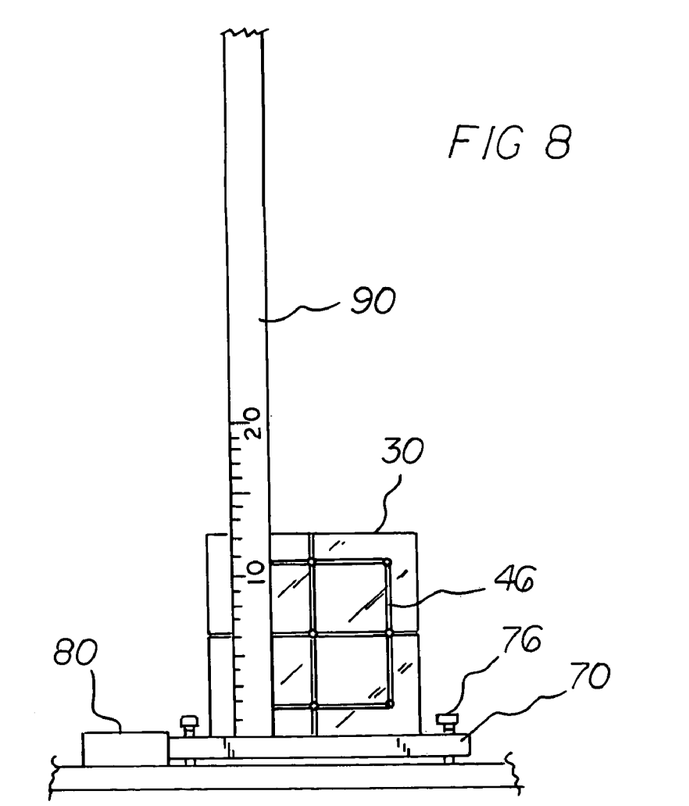
FIG. 8 is a side elevational view similar to FIG. 1 but with the ruler measuring discrepancies.
Figure 9:
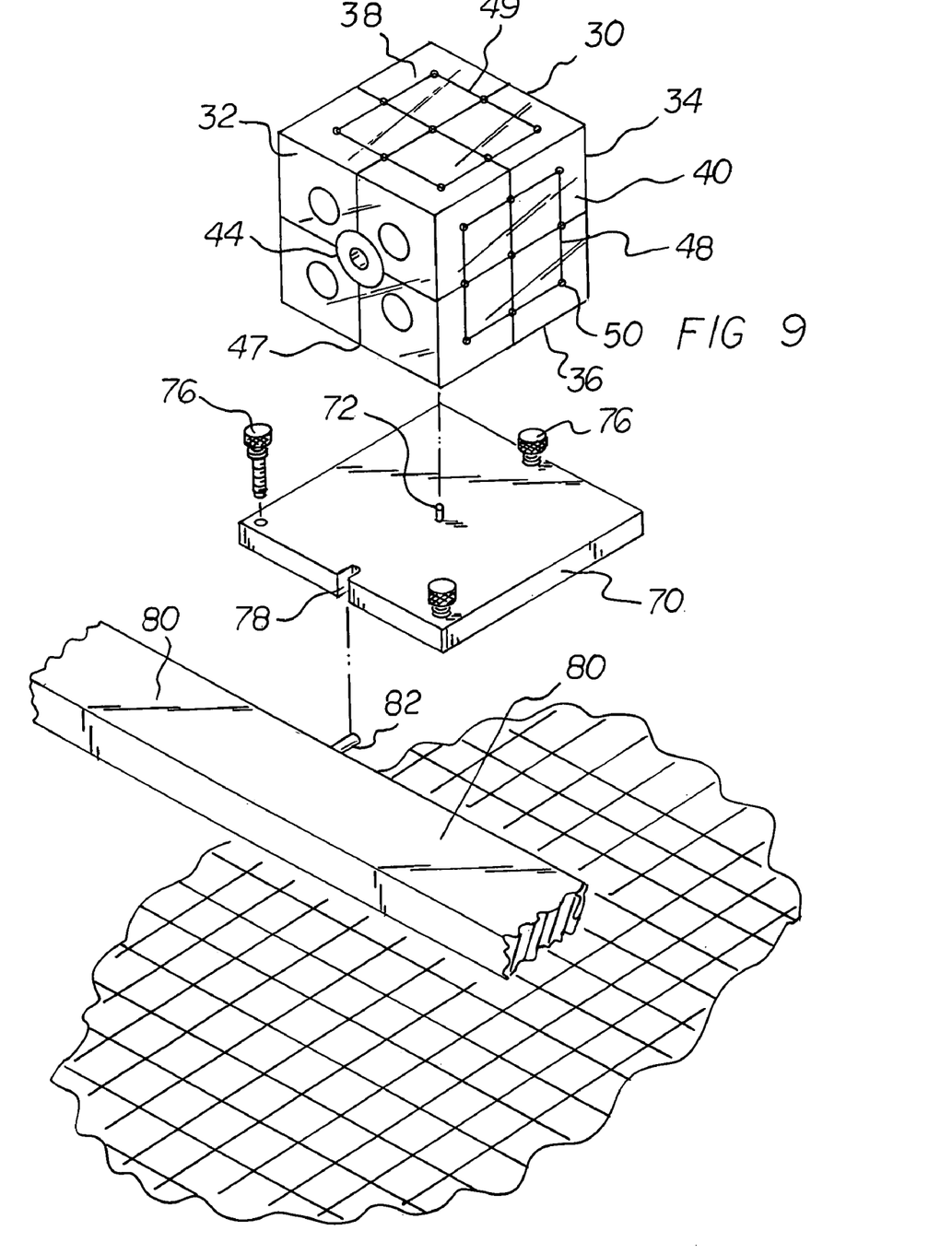
FIG. 9 is an exploded perspective view of the system of the prior Figures.

Next provided is a ruler 90. The ruler is configured with indicia to enable the user to measure any discrepancies between a projected beam and the central and peripheral grid lines of the cube, thereby allowing for re-centering of the components.

Next provided is a universal machine alignment tool 100. The tool provides a way to achieve a standard centering on any one of a class of commercially available patient resting surfaces, which includes X-ray table surfaces, CT scanning table surfaces and MRI scanning table surfaces. The tool has a central locking component 102. The central locking component has a flat lower portion with an upper surface and a lower surface. The central locking component has two sides 104 and two top lips 106. The central locking component has an upwardly opened C-shaped configuration with the two sides. Each side has an upper end and a lower end and are oppositely located and upwardly projecting. The lower end of each of the sides is coupled with the flat lower portion of the central locking component. The top end of each of the sides has a top lip. The top lips are oppositely located. The C-shaped configuration of the central locking component forms a rectangularly shaped passageway 108 there through. The flat lower portion of the central locking component has two threaded upwardly projecting locking lug studs 110. The upper surface of the lower portion has a plurality of indicia 112 and a centrally located alignment pin aperture 114. The alignment tool has a pair of table side end clamps 116 with each clamp having a generally T-shaped configuration. There is a flat table edge lip 118 coupled at right angles to a rectilinearly shaped adjustable portion 120. Each adjustable portion has a slot 122 there through. The alignment tool has a pair of locking lug nuts 124 sized to be received by the threaded locking lug studs of the flat lower portion of the central locking component.

Figure 4:
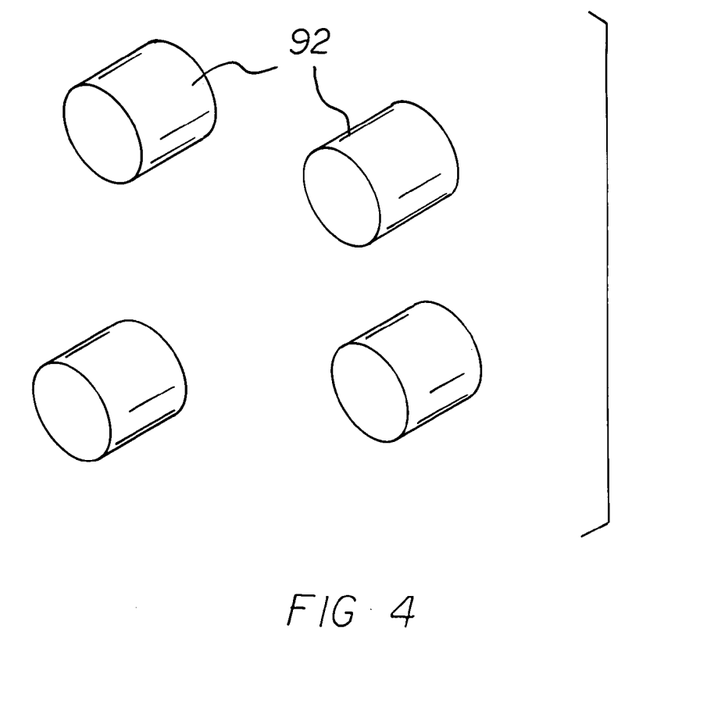
FIG. 4 is a perspective view of the density plugs.

Lastly, there is provided a plurality of density plugs 92. The density plugs each have a density to imitate the density of a various body compartment. A first density plug has the density of bone. A second density plug has the density of water. A third density plug has of the density of an inflated lung. A fourth density plug has the density of a deflated lung. The use of the density plugs thereby allows a user to test a beam's strength against a standard density.

Figure 12:
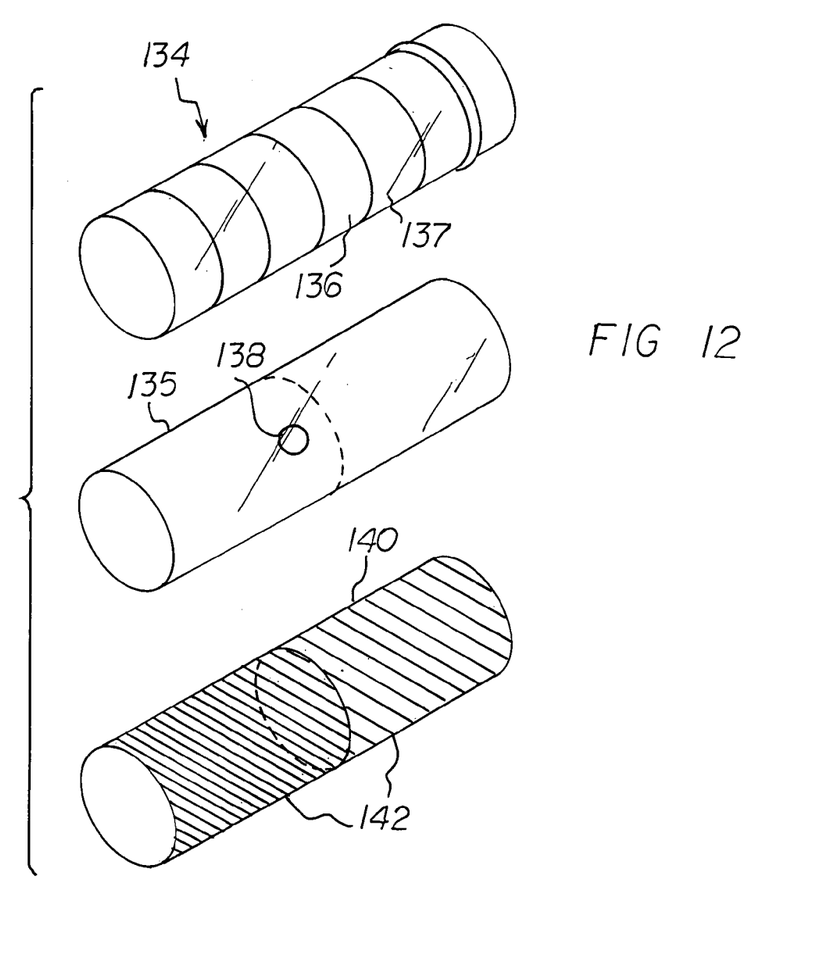
FIG. 12 is an illustration of the density plug and alternate embodiments of the plug.

In an alternate embodiment there may be provided a plug 139 having a liquid filled center enclosing a test ball 132 there in.

In another alternate embodiment there may be provided a density plug 134 which would have a plurality of tissue densities 136 represented there in as a means of calibrating a machine by providing electron density values for a given tested machine.

In yet another alternate embodiment of the system, a plug 135 may be provided with the plug having a tungsten ball 138 located therein, the use of a tungsten ball allowing the calibration of stereotactic diagnostic and treatment machines.

In yet another alternate embodiment of the system, a plug 140 may be provided with high/low resolution calibration densities 142 incorporated there in.

The present invention was designed to provide an easy low cost approach to the daily and monthly quality assurance tasks for therapists and physicists. The present invention will aid in verifying the geometric beam position accuracies with other systems within a department. Furthermore, the present invention provides the physicist and dosimetrist the ability to verify electron beam density values produced by a computer tomography, or CT, machine.

In the test procedure in which this system is used, the four unique density inserts are quickly scanned then the image is transferred to the radiation therapy department, or RTP, for verification of the electron density values of the bone, water, inhale and exhale density inserts. Comparing the slice values to the known density values, the user can quickly verify CT image density values for treatment planning, thereby assuring quality of care.

Additionally, the present invention provides an internal known-object insert that is scanned with the CT simulator. With the known-object multiple image slice set, the user creates a treatment plan/virtual simulation plan of the object for size and location verification of the treatment beam position alignment.

Other inserts provided will give the physicists the ability to quickly measure single point expected dose values against a controlled and known value, without using additional phantom devices.

The present invention provides the user the ability to scan, plan and verify the exported radiotherapy beam designs of the intended treatment field. The system allows the user to verify that the dose prescribed is the dose delivered. The system also allows the user to verify that the dose delivered is delivered to the exact location it is needed in.

A sample generic quality assurance process is as follows. The user verifies the position of the phantom on a treatment surface. The invention is centered in the X and Y position of the scan plane. The phantom is scanned after the user has verified the position of the cube. This is accomplished by physically moving the present invention and verifying its position with the imaging tool set supplied with the scanner.

The operator verifies the tilt of gantry tilt is at a "O" degree tilt in respect to front surface of the present invention. Once aligned correctly, the user scans the present invention at 1 mm increments throughout the entire phantom body. Then, the user creates a 10 cm×10 cm RTP/virtual simulation plan for export to the beam marking system, such as a laser, position verification. The user then compares the expected field positions with the actual beam field illuminated positions. These positions are verified on three external sides of the present invention. Additionally, the internal object located in the exact center axis position of the present invention provides an additional beam position quality assurance verification. The user then sets up the present invention on the treatment machine. The user can verify lasers/field lights and the expected treatment dose by using an electrometer and the dose chamber insert.

Benefits attained by the use of the present invention include two 1 mm wide alignment verification grooves on the surface of the machine. These provide for easy viewing and quick alignment checks of laser or aiming beam positions. Multi-use quality assurance programs within the therapy department can use the present invention.

The present invention provides the ability to verify scanned image set position alignment from the radiology department to the radiation therapy department for verification prior to a laser marking process. Precision 10 cm×10 cm. fixed beam fields on three surfaces of the present invention allow for exact image and beam geometric design quality assurance verification. An easy leveling base is provided for setting up an exact level plane for the qualify assurance process from machine to machine.

The present invention provides a single slice check for laser-offset verification with standard CT scanner and/or CT simulator. Treatment machine quality assurance for lasers, mechanicals, and beam geometry are provided.

The four electron density inserts provide the user with the ability to easily verify the electron densities values produced on the CT simulator for qualify assurance review. This is of particular benefit when determining the consistency of electron density values from week to week. The four inserts are: Bone (+800), $H_2O$ (0.0), Inhaled Lung (−800), and Exhaled Lung (−500) and Water (O). This verification is useful in providing a repeatable and dependable quality assurance for in-house testing methodology. This qualify assurance task can be accomplished daily, weekly, monthly and annually by normal radiotherapy staff members.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A medical device standardizing system comprising, in combination:
 a cubic test device formed of a transparent material having a front face, a rear face, a bottom face, a top face and a pair of side faces, each being equally sized and each having an edge, each face of the six faces of the cube having a pair of etched lines also known as the central grid lines being a first distance from the cube edge, the lines thereby dividing the face up into four equally sized squares, the lines being perpendicular to each other and are equally spaced from the edges of the cube, the central grid lines intersecting in the center point of each of the faces of the cube thereby dividing each of the cube faces into four quadrants, the cube having a centrally located notch on the lower edge of the cube side, the central grid line meeting the edge of the cube at the notch thereby indicating the mid-point of that face, the face of the cube also having four peripheral grid lines etched there into, the lines being at right angles to each other and parallel to the edge and a second distance from the edge of the cube, with the peripheral grid lines intersecting near the four corners of the face of the cube, on each of the faces, the grid lines being equidistant from the edge of the cube whereby a plurality of squares are formed on the cube face where the peripheral grid lines intersect each other and intersect the central grid lines, with the front face having a centrally located cylindrical aperture extending all the way to the rear face forming an aperture there through, the rear face of the test cube device also has four equally spaced recesses there into, with the recesses being configured to receive and hold any one of a plurality of density plugs, the destination plugs each have a specific density to mimic specific tissue density, with the test device also having a plurality of small bores, known as pin holes, positioned at all intersections of the central and peripheral grid lines;
 a probe cylinder being configured to be received by and held within the central aperture, the probe cylinder being configured to receive a probe of a radiation detecting and measuring device, the probe clylinder being configured and sized to couple within the central cylindrical aperture of the cubic test device;
 a test device resting table having a flat plane surface to receive the cubic test device, the flat plane surface also having a plurality of indicia to enable a user to locate the test cube in the center of the resting table, the resting table having a first central finger configured to couple with a central bore on the bottom face of the cubic test device to prevent the cubic test device from sliding on the resting table, the resting table having a plurality of leveling screws and a recess aperture on one side;
 a test device level having a generally rectilinear configuration with an upper surface and a lower surface and two opposing ends with an edge disposed there between, the level having a plurality of sized recesses therein on the upper surface of each end of the level, the recesses enclosing a round radio-opaque sphere, the level also having a recess on each end with an enclosed radio-opaque pin contained therein with the ends each having indicia inscribed thereon, the level having a second central finger to couple with the recess aperture of the resting table to hold the resting table in place, the level having a pair of studs coupled to the lower surface of the level, the studs each having an associated o-ring coupled thereto;
 a ruler being configured with indicia to enable the user to measure any discrepancies between a projected beam and the scored white central and peripheral grid lines of the cube thereby allowing for re-centering of the appropriate components;
 a machine alignment tool to provide a standard centering on a patient resting surface of an X-ray table, CT scanning table and MRI scanning table, the tool having a central locking component having a flat lower portion with an upper surface and a lower surface, the central locking component having two sides and two top lips, the central locking component having an upwardly opened C-shaped configuration with the two sides each having an upper end and a lower end and being oppositely located and upwardly projecting with the lower end of each of the sides being coupled with the flat lower portion of the central locking component with the top end of each of the sides having a top lip, the top lips being oppositely located, with the C-shaped configuration of the central locking component forming a rectangularly shaped passageway there through, the flat lower portion of the central locking component having two threaded upwardly projecting locking lug studs with the upper surface of the lower portion having a plurality of indicia and a centrally located alignment pin aperture, the alignment tool having a pair of table side end clamps with each clamp having a generally T-shaped configuration with a flat table edge lip coupled at right angles to a rectilinearly shaped adjustable portion, each adjustable portion having a slot there through, the alignment tool having a pair of locking lug nuts sized to be received by the threaded locking lug studs of the flat lower portion of the central locking component; and the plurality of density plugs having a varying of densities to imitate the density of various body compartments, with one density plug having the density of bone; a second density plug having the density of water, a third density plug having of the density of an inflated lung and a fourth density plug having the density of a deflated lung, thereby allowing a user to test a beam's strength against a standard density.

2. A medical device standardizing system comprising, in combination:

a cubic test device having a centrally located cylindrical aperture there through, from one side to the opposite side, the cubic test device further comprising a plurality of etched lines being located on each face of the six faces of the cube, with each face having a pair of etched lines also known as the central grid lines being a first distance from the cube edge, the lines thereby dividing the face up into four equally sized squares, and a centrally located notch on the lower edge of the cube side, each face of the cube also having four peripheral grid lines etched there into, the lines parallel to the respective cube edge with the peripheral grid lines intersecting near the four corners of the cube on each of the faces, with the front face having the centrally located cylindrical aperture there through, the rear face of the test cube device also has four equally spaced recesses there into, the recesses configured to receive and hold any one of a plurality of density plugs;

a probe cylinder configured to receive a probe of a cylindrical radiation detector and being configured to be received by and held within the central cylindrical aperture;

a test device resting table having a flat plane surface to receive the cubic test device;

a test device resting table level;

and a machine alignment tool having a central locking component, the central locking component having an upwardly open C-shaped configuration slidably configured to clamp the cubic test device to the flat plane surface.

3. A medical device standardizing system as described in claim 2 wherein the cubic test device further comprises a plurality of small bores, known as pin holes, positioned at all intersections of the central and peripheral grid lines.

4. A medical device standardizing system as described in claim 2 wherein each of the plurality of density plugs, has a density to imitate tissue density.

5. A medical device standardizing system as described in claim 4 wherein, each of the density plugs has a density to imitate tissue density with a first density plug having the density of bone, a second density plug having the density of water, a third density plug having of the density of an inflated lung and a fourth density plug having the density of a deflated lung, thereby allowing a user to test a beam's strength against a standard density.

* * * * *